United States Patent [19]
Croze et al.

[11] Patent Number: 5,141,865
[45] Date of Patent: Aug. 25, 1992

[54] MONOCLONAL ANTIBODIES WHICH BIND THROMBOXANE A2 RECEPTOR ANTAGONISTS AND DIAGNOSTIC METHODS BASED THEREON

[75] Inventors: Edward M. Croze, San Ramon, Calif.; Jan-I Tu, Kendall Park, N.J.

[73] Assignee: E. R. Squibb & Sons, Inc., Princeton, N.J.

[21] Appl. No.: 438,548

[22] Filed: Nov. 17, 1989

[51] Int. Cl.$^5$ .................. C12N 5/20; C07K 15/28
[52] U.S. Cl. ..................... 530/388.9; 435/70.21; 435/172.2; 435/7.92; 435/240.27; 435/188; 436/542; 424/85.8
[58] Field of Search ............. 424/85.8, 88; 435/7.92, 435/70.21, 172.2, 240.21; 436/542; 514/381; 530/387–389

[56] References Cited

U.S. PATENT DOCUMENTS 4,663,336  5/1987  Nakane et al. .................. 514/381
4,975,279 12/1990  Schumacher et al. ............. 424/94

OTHER PUBLICATIONS

G. Kohler et al., Nature 256, 495–497 (1975).
M. Reinke et al., FEBS Letters 232, 46–50 (1988).
Jaqoda et al., "A Specific Radioimmunoassay for the Measurement of a New Thromboxane Antogonist, SQ 30,741, in Plasma," *Clin. Chem.* 35(6): 1189, 1989.
Reinke et al., "A Monoclonal Anti-Thromboxane Bz Antibody," *FEBS Letters* 232(1):46–50, 1988.

*Primary Examiner*—John Doll
*Assistant Examiner*—Robert D. Budens
*Attorney, Agent, or Firm*—James M. Bogden

[57] ABSTRACT

Monoclonal antibodies which bind thromboxane A2 receptor antagonists, hybrid cell lines which produce these monoclonal antibodies, and immunoassay methods for detecting thromboxane A2 receptor antagonists using these monoclonal antibodies.

15 Claims, 1 Drawing Sheet

MONOCLONAL ANTIBODIES WHICH BIND THROMBOXANE A2 RECEPTOR ANTAGONISTS AND DIAGNOSTIC METHODS BASED THEREON

BACKGROUND OF THE INVENTION

The fusion of mouse myeloma cells to spleen cells from immunized mice by Kohler and Milstein in 1975 [Nature 256, 495–497 (1975)] demonstrated for the first time that it was possible to obtain continuous cell lines making homogeneous (so-called "monoclonal") antibodies. Since this seminal work, much effort has been directed toward the production of various hybrid cell lines (also called "hybridomas") and to the use of the antibodies made by these hybridomas for various scientific investigations. While the general technique for the preparation of hybridomas and monoclonal antibodies is well-known, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity.

The present invention concerns monoclonal antibodies which bind thromboxane A2 receptor antagonists, hybrid cell lines which produce these monoclonal antibodies and immunoassay methods for detecting thromboxane A2 receptor antagonists using these monoclonal antibodies.

SUMMARY OF THE INVENTION

The present invention comprises hybridoma cell lines which produce monoclonal antibodies which bind thromboxane A2 receptor antagonists.

The present invention further comprises monoclonal antibodies which bind thromboxane A2 receptor antagonists.

The present invention additionally comprises immunoassay methods for detecting the presence of thromboxane A2 receptor antagonists in a sample.

The present invention also comprises immunoassay methods for quantitatively determining the amount of thromboxane A2 receptor antagonists in a sample.

DETAILED DESCRIPTION OF THE INVENTION

Figure 1:
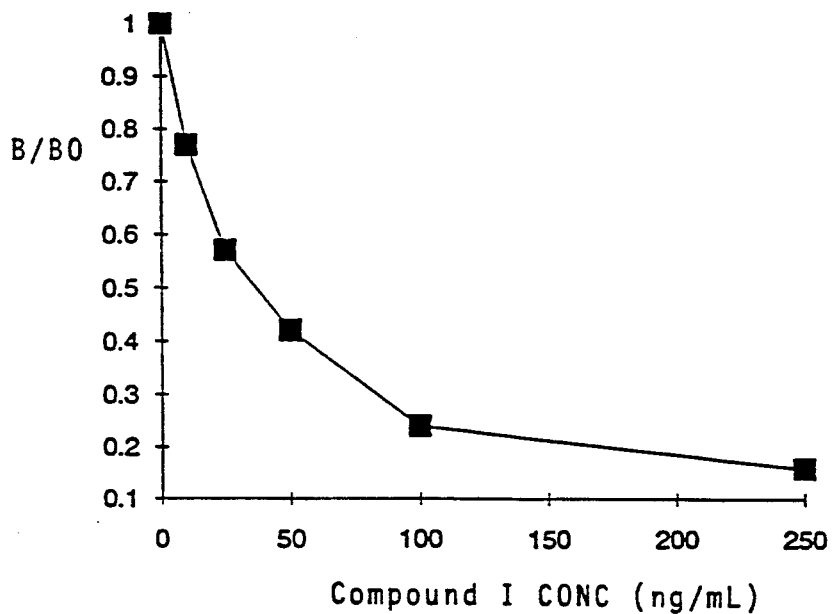
FIG. 1 shows a standard curve for the assay of Compound I using a monoclonal antibody (MCTX1) which recognizes a thromboxane A2 receptor antagonist.

The present invention concerns hybrid cell lines, monoclonal antibodies and immunoassay methods utilizing these antibodies.

In particular, the present invention comprises hybrid cell lines which produce monoclonal antibodies which bind thromboxane A2 receptor antagonists.

Particularly preferred are hybrid cell lines which produce monoclonal antibodies which bind to the thromboxane A2 receptor antagonist [1S-[1β,2α(5Z)-,3α,4β]]-7-[3-[[[[(1-oxoheptyl)amino]acetyl]amino]methyl]-7-oxabicyclo[2.2.1]hept-2-yl]-5-heptenoic acid, whose structure is shown in Table 1, and which is sometimes hereinafter referred to as Compound I.

TABLE 1

STRUCTURES OF COMPOUND I, IMMUNOGEN AND RADIOLABEL-1

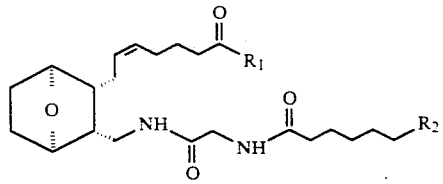

| COMPOUND | $R_1$ | $R_2$ |
|---|---|---|
| Compound I | —OH | —CH$_3$ |
| Immunogen | —NH—BSA | —CH$_3$ |
| Radiolabel-1 | —NH—CH$_2$—CH$_2$— 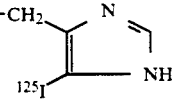 | —CH$_3$ |

Additionally preferred are hybrid cell lines which produce monoclonal antibodies which bind to derivatives of Compound I, for example esters or salts, as disclosed in U.S. Pat. No. 4,663,336, or metabolites of Compound I.

Also preferred is a hybrid cell line designated as HYTX, or hybrid cell lines which have the identifying characteristics of HYTX.

Hybridoma HYTX was deposited with the American Type Culture Collection, Rockville, Md. on Sep. 22, 1989 under the Budapest Treaty and assigned ATCC accession no. HB 10235.

The term thromboxane A2 receptor antagonist as used in this application means a compound related to but different in structure from thromboxane which binds specifically to the thromboxane A2 receptor and counteracts the action of thromboxane and thromboxane agonists.

The hybrid cell lines of the present invention may be produced by various methods generally known to those of ordinary skill in the art. In general, the method involves immunizing suitable mammals, for example BALB/c mice, with the antigen of interest, in this case a thromboxane A2 receptor antagonist, fusing antibody producing cells isolated from the spleen of the animal with myeloma cells, cloning the resulting hybrid cells and selecting those cells which produce the desired monoclonal antibody which binds the antigen of interest.

Immunizations are usually performed with purified antigens. In the case of relatively low molecular weight antigens (haptens) such as thromboxane A2 receptor antagonists, immunizations are usually performed using the hapten conjugated to a carrier molecule, for example, heat-denatured bovine serum albumin (BSA). Various conjugation procedures may be used to conjugate haptens to carrier molecules. For example, an activated ester of a hapten may be prepared by reacting the hapten with 1-ethyl-3-(3-dimethylaminopropyl)carbodiimide and N-hydroxysuccinimide. The conjugate may then be prepared by reacting the activated ester of the hapten with the carrier molecule in a mildly alkaline solution. Alternatively, glutaraldehyde may be employed to conjugate haptens to carrier molecules.

The usual mammals used for immunizations are mice, especially BALB/c mice, but other mammals and mouse strains may also be employed. The immunizations are performed in a manner known in the art, such as by administering parenterally, intraperitoneally, intravenously and/or subcutaneously, three to six injections each containing an appropriate amount of purified antigen (i.e., from about 1 μg to about 50 μg), at intervals of about one to six weeks, usually together with an adjuvant that stimulates the production of lymphocytes, for example, complete or incomplete Freund's adjuvant. While immunizations are generally performed in vivo, various in vitro procedures are also known.

Antibody-producing cells of the immunized animals present in the spleen are taken from the animals two to six days after the last ("booster") immunization and fused with myeloma cells of a suitable cell line. Myeloma cell lines and cell lines derived therefrom are known as suitable fusion partners. The myeloma cell line is generally derived from the same species as the immunized mammal, since intra-species hybrids are more viable than inter-species hybrids. Myeloma cells that lack the enzyme hypoxanthine-guaninephosphoribosyl transferase (HGPRT) or the enzyme thymidine kinase (TK) and that, for that reason, do not survive in a selective culture medium containing hypoxanthine, aminopterin and thymidine (HAT medium), may be employed. Myeloma cells and cell lines prepared therefrom that do not survive in HAT medium and do not secrete any immunoglobulins or parts thereof, for example cell lines X63-Ag8.653 and Sp2/0-Ag14, may also be used. Various fusion-promoters, for example, Sendai virus or other paramyxoviruses, optionally in UV-inactivated form, calcium ions, surface-active lipids, such as isolecithin, or polyethylene glycol may also be employed. Myeloma cells are usually fused with a three- to twenty-fold excess of spleen cells from immunized animals in a solution containing from about 30 to 50% polyethylene glycol (PEG) having a molecular weight of about 1000 to 4000. Exposure to PEG for about 2 to 3 minutes appears to be optimal to prevent toxicity to the cells; temperatures of about 37° C. are recommended.

After fusion, the cells are partitioned out and cultured in selective HAT medium, with only hybrid cells surviving, since these combine, from the myeloma cells, the ability to grow in vitro and, from the antibody-producing cells of the immunized animals, ht emissing HGPRT or TK genes and, therewith, the ability to survive in HAT medium.

Suitable culture media for the growth of the hybrid cells are the customary standard culture media, for example, Dulbecco's Modified Eagles Medium or Roswell Park Memorial Institute (RPMI) 1640 medium containing 10–15% fetal calf serum and supplemental with antibiotics. At the beginning of cell growth, so-called feeder cells, for example normal mouse peritoneal exudate cells, spleen cells, bone marrow macrophages or the like, may be added. At regular intervals, the culture media may be supplemented by selective HAT medium to prevent hybrid cells from being overgrown by ordinary myeloma cells.

The cell culture supernatants of the hybrid cells surviving HAT selection are examined for the presence of the desired monoclonal antibodies. Advantageously, the cell supernatants are tested in an immunoassay, for example, radioimmunoassay or enzyme immunoassay, that demonstrates the binding of monoclonal antibodies to the antigen of interest.

Those hybridomas which produce antibodies having the desired specificity as well as other desirable characteristics can then be maintained as viable cultures and/or frozen for storage.

The present invention further comprises monoclonal antibodies which bind thromboxane A2 receptor antagonists.

Particularly preferred are monoclonal antibodies which bind the thromboxane A2 receptor antagonist [1S-[1β,2α(5Z),3α,4β]]-7-[3-[[[[(1-oxoheptyl)amino] acetyl]amino]methyl]-7-oxabicyclo [2.2.1]hept-2-yl]-5-heptenoic acid (Compound I).

Additionally preferred are monoclonal antibodies which bind to derivatives of Compound I, for example esters or salts, as disclosed in U.S. Pat. No. 4,663,336, or metabolites of Compound I.

Also preferred is the monoclonal antibody designated as MCTX1, or a monoclonal antibody with the identifying characteristics of the monoclonal antibody designated as MCTX1.

Particularly preferred is the monoclonal antibody designated as MCTX1 which has been substantially purified.

Additionally preferred are derivatives of the monoclonal antibody designated as MCTX1.

The monoclonal antibodies of the present invention may be produced by various methods generally known to those of ordinary skill in the art. Hybrid cells producing such antibodies may be cultured in vitro and the monoclonal antibodies isolated from the cell culture supernatants, or may be multiplied in vivo in a suitable mammal, and the monoclonal antibodies isolated from the body fluids of that mammal. If desired, a monoclonal antibody resulting from either of these techniques may be converted into a derivative thereof.

Suitable culture media for in vitro culturing are the customary standard culture media, for example, Dulbecco's Modified Eagles Medium or RPMI 1640 medium containing 10 to 15% fetal calf serum and supplemented with antibiotics.

Large quantities of the desired monoclonal antibodies may also be obtained by multiplying the hybridoma cells in vivo. For this purpose, antibody producing hybridomas are inoculated intraperitoneally into syngeneic mammals, and after 1 to 3 weeks, the antibodies are isolated from the ascites fluid of those mammals. For example, hybrid cells originating from BALB/c mice are injected intraperitoneally into BALB/c mice that have previously been pretreated intraperitoneally with a hydrocarbon such as 2,6,10,14-tetramethylpentadecane (pristane) to prevent fluid drainage from the intraperitoneal cavity, and, after 8 to 10 days, ascites fluid is taken from these animals.

The monoclonal antibodies produced in vitro or in vivo may be purified using various methods, for example, gel filtration chromatography, ion-exchange chromatography, DEAE-cellulose chromatography or affinity chromatography. Optionally, selected proteins in the culture supernatants or ascites fluid, including the desired monoclonal antibodies, may be precipitated using specific concentrations of ammonium sulphate or the like before being subjected to chromatography. Particularly preferred for MCTX1 is a purification process involving chromatography on a CM Affi-Gel Blue column followed by affinity-chromatography on a recombinant-Protein G Sepharose 4B column.

If desired, derivatives of the monoclonal antibodies produced either in vitro or in vivo may be prepared.

Derivatives of monoclonal antibodies according to the invention include, for example, fragments, such as Fab, Fab' or F(ab')$_2$ fragments, that retain their specificity for the antigenic determinants of the antigen of interest, radioactively labelled monoclonal antibodies which are labelled, for example, with radioactive iodine ($^{125}$I, $^{131}$I) carbon ($^{14}$C), sulphur ($^{35}$S), tritium ($^3$H) or the like, and monoclonal antibody conjugates with enzymes such as horseradish peroxidase, alkaline phosphatase, $\beta$-D-galactosidase, glucose oxidase, glucoamylase, carbonic anhydrase, acetylcholinesterase, lysozyme, malate dehydrogenase or glucose-6-phosphate dehydrogenase. Additional derivatives include monoclonal antibodies labeled with fluorescent materials such as fluorescein and rhodamine, and monoclonal antibodies labeled with biotin.

Fragments of monoclonal antibodies according to the invention, for example, Fab, Fab' or F(ab')$_2$ fragments, that retain their specificity for the antigenic determinants of the antigen of interest, may be prepared according to generally known methods, for example, by fragmenting monoclonal antibodies through proteolytic digestion with enzymes such as pepsin or papain and/or by cleavage of disulphide bonds by chemical reduction.

Monoclonal antibodies radioactively labelled with iodine ($^{125}$I, $^{131}$I) may be obtained by iodination, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. Radioactively labelled monoclonal antibodies according to the invention may also be prepared by adding to the culture media for the in vitro culturing, in a known manner, radioactively labelled nutrients containing radioactive carbon ($^{14}$C), tritium ($^3$H), sulphur ($^{35}$S) or the like, for example, L-($^{14}$C)-leucine, L-($^3$H)-leucine or L-($^{35}$S)-methionine, and obtaining the monoclonal antibodies as described above.

Enzyme-labelled monoclonal antibodies according to the invention may be obtained by various generally known methods, for example, by reacting monoclonal antibodies and the desired enzyme with coupling reagents such as aldehydes, carbodiimides, maleimides, imidates, succinimides and pyridyl disulfides. Specific coupling agents include, for example, glutaraldehyde, periodate, N,N'-o-phenylenedimaleimide, N-(m-maleimidobenzoyloxy)-succinimide, and N-(3-(2'-pyridyldithio)-propionoxy)-succinimide or the like.

Various enzyme substrates, for example 5-aminosalicyclic acid, 0-phenylenediamine, 3,3'-dimethoxybenzidine, and 2,2'-azino-bis-(3)-ethylbenzothiazolin-6-sulphonic acid for horseradish peroxidase and p-nitrophenyl phosphate for alkaline phosphate, may be used in conjunction with the enzyme-labelled antibodies.

It is contemplated that the present invention encompasses all monoclonal antibodies exhibiting the characteristics of monoclonal antibody MCTX1 described herein. It was determined that antibody MCTX1 belongs to the subclass IgG. It is contemplated that antibodies having the patterns of reactivity illustrated herein are included within the subject invention regardless of the immune globulin class or subclass to which they belong. For example, a monoclonal antibody exhibiting the characteristic described herein may be of class IgG$_1$, IgG$_{2a}$, IgG$_{2b}$, or IgG$_3$, or of classes IgM, IgA, or of other known Ig classes.

Furthermore, since the hybrid cell line produced from a known mouse myeloma cell line and spleen cells from a known species of immunized mouse cannot be further identified except by reference to the antibody produced by the hybrid cell line, it is contemplated that all hybrid cell lines producing antibodies having the reactivity characteristics described above are included within the subject invention.

The present invention further comprises immunoassay methods utilizing monoclonal antibodies and derivatives thereof which bind thromboxane A2 receptor antagonists for the qualitative and quantitative determination of thromboxane A2 receptor antagonists, especially in biological fluids.

Particularly preferred is a qualitative immunoassay method for detecting the presence of a thromboxane A2 receptor antagonist in a sample comprising:

(a) incubating the sample with a monoclonal antibody which binds to the thromboxane A2 receptor antagonist; and (b) detecting the presence of immune complexes formed by the thromboxane A2 receptor antagonist and the monoclonal antibody.

Additionally preferred is an immunoassay method for quantitatively determining the amount of a thromboxane A2 receptor antagonist in a sample comprising:

(a) incubating the sample with a monoclonal antibody which binds to the thromboxane A2 receptor antagonist;

(b) determining the amount of immune complexes formed by the thromboxane A2 receptor antagonist and the monoclonal antibody; and (c) correlating the amount of immune complexes formed with the amount of thromboxane A2 receptor antagonist present in the sample.

The immunoassay methods of the present invention may be a radioimmunoassay (RIA) which utilizes, depending upon the particular protocol employed, unlabelled or radioactively labelled derivatives of monoclonal antibodies which bind thromboxane A2 receptor antagonists, either alone or in combination. In the case where the thromboxane A2 receptor antagonist binding monoclonal antibody is unlabeled, a different detectable marker, for example, a radiolabelled thromboxane A2 receptor antagonist derivative, may be employed. Any of the known modifications of RIA, for example, homogeneous RIA, heterogeneous RIA, competitive RIA, and sandwich RIA may be employed. Particularly preferred is a competitive, heterogeneous RIA. In the preferred assay, a monoclonal antibody which binds a thromboxane A2 receptor antagonist is incubated with a sample and a radiolabelled derivative of the thromboxane A2 receptor antagonist. After separating unbound radiolabelled derivative from antibody-bound radiolabelled derivative, the amount of antibody bound or unbound radioactivity is measured, and correlated with the amount of thromboxane A2 receptor antagonist in the sample.

The immunoassay method of the present invention may also be an enzyme immunoassay (EIA) which utilizes, depending upon the particular protocol employed, unlabelled or enzyme-labelled derivatives of monoclonal antibodies which bind thromboxane A2 receptor antagonists, either alone or in combination. In the case where the thromboxane A2 receptor antagonist binding monoclonal antibody is not enzyme-labelled, a different detectable marker, for example, an enzyme-labelled antibody capable of binding to the thromboxane A2 receptor antagonist binding monoclonal antibody, may be employed. Any of the known modifications of EIA, for example, enzyme-linked immunoabsorbant assay (ELISA), may be employed. Particularly preferred is an indirect ELISA. In the preferred assay, a sample is incubated with a monoclonal antibody which binds a thromboxane A2 receptor antagonist and the thromboxane A2 receptor antagonist conjugated to a carrier protein and immobilized on a solid support. Any of the common supports used in immunoassays may be employed. Suitable solid supports include, for example, the inner walls of glass tubes and polystyrene based microtiter plates, or solid particles made from various materials such as polypropylene, polystyrene, polyethylene and glass. During this step, some of the monoclonal antibody which binds the thromboxane A2 receptor antagonist becomes bound to the immobilized carrier conjugated thromboxane A2 receptor antagonist. Any substances in the sample which do not bind to the immobilized carrier conjugated thromboxane A2 receptor antagonist (e.g., thromboxane A2 receptor antagonist in sample) during this incubation step are separated from the solid support. The solid support is then contacted with a enzyme-labelled second antibody which is capable of binding to the specific monoclonal antibody which is bound to the immobilized, carrier conjugated, thromboxane A2 receptor antagonist. After separation of any unbound enzyme-labelled second antibody from the solid support, the solid support is contacted and incubated with an enzyme substrate capable of reacting with the enzyme or the enzyme-labelled antibody to produce a detectable reaction product. The product of the enzymatic reaction is then measured and correlated with the amount of thromboxane A2 receptor antagonist in the sample.

The immunoassay method of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidinbiotin or strepavidin-biotin detection system.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. The amount of thromboxane A2 receptor antagonist binding antibody used is typically selected to give 50% binding of detectable marker in the absence of sample. For example, in the preferred RIA, the amount of antibody used is selected to give 50% binding of radiolabelled thromboxane A2 receptor antagonist when the assay is performed in the absence of sample thromboxane A2 receptor antagonist. If purified antibody is used, the amount of antibody will generally range from about 10 ng to about 50 ng. Typical assay conditions include a temperature range of about 4° C. to about 45° C., preferably about 25° C., a pH valve range of about 5 to 9. preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins. stabilizers, biocides and non-ionic detergents may also be included.

The immunoassay methods of the present invention utilizing monoclonal antibodies are especially useful for monitoring the presence or amount of a thromboxane A2 receptor antagonist or its metabolites in the bodily fluids, for example saliva, serum and urine, of a human patient being treated with the thromboxane A2 receptor antagonist.

The monoclonal antibodies of the present invention may also be used to purify thromboxane A2 receptor antagonists. Briefly, monoclonal antibodies which bind a thromboxane A2 receptor antagonist may be immobilized on a solid support, and contacted with a material (e.g., solution) containing the thromboxane A2 receptor antagonist under conditions permitting the monoclonal antibodies to bind the thromboxane A2 receptor antagonist. Any unbound material is separated from the immobilized monoclonal antibodies, and the bound thromboxane A2 receptor antagonist eluted from the monoclonal antibodies with a suitable eluant to yield purified thromboxane A2 receptor antagonist.

The following examples are further illustrative of the present invention. These examples are not intended to limit the scope of the present invention and provide further understanding of the invention.

EXAMPLE I

Cell Culture

Cell culture media and supplies were obtained from Gibco Laboratories (Life Technologies, Inc., Grand Island, N.Y.) unless otherwise indicated. A mouse $SP_2/O$ myeloma (plasmacytoma), hypoxanthine guanine phosphoriboxyl transferase (HGPRT) deficient cell line was purchased from NIGMS Human Genetic Mutant Cell Repository (Camden, N.J.). $SP_2/O$ cells and selected hybridomas were cultured at 37° C. in a 5% $CO_2$ atmosphere in Dulbecco's Modified Eagles Medium (DMEM) supplemented with 10% fetal calf serum, fungizone (100 µg/l), L-glutamine (0.3 mg/ml) and antibiotics (gentamycin, 0.25 mg/ml; kanamycin, 0.1 mg/ml; penicillin, 100 U/ml; streptomycin, 0.1 mg/ml)(DMEM complete). After fusion, cells were grown in DMEM complete containing HAT (hypoxanthine, 0.1 mM; aminopterin, 0.1 µM; thymidine, 0.016 mM), including a 10-fold dilution of HCF (hybridoma cloning factor) sold under the trademark ORIGEN by IGEN, Inc. (Rockville, Md.).

EXAMPLE II

Production of Monoclonal Antibodies

Immunizations were performed with Compound I conjugated to heat denatured bovine serum albumin (BSA) (Immunogen), the structure of which is shown in Table 1.

Compound I may be prepared according to the methods described in U.S. Pat. No. 4,663,336, the specification of which is incorporated herein by reference.

In order to prepare immunogen, a sample of Compound I (9.9 mg, $2.3 \times 10^{-2}$ mmol) spiked with 14C-labelled Compound I as a tracer (1.1 mg, $2.7 \times 10^{-3}$ mmol) was dissolved in 0.5 ml of dimethylformamide and cooled in an ice bath. To this was added N-hydroxysuccinimide (6.1 mg, $5.3 \times 10^{-2}$ mmol) and 1-ethyl-3-(3-dimethylaminopropyl)carbodiimide (10.1 mg, $5.3 \times 10^{-2}$ mmol). The resulting solution was brought to room temperature and stirred for 2 hours, then added dropwise to a solution of heat treated bovine serum albumin (20.0 mg, $3.1 \times 10^{-4}$ mmol) dissolved in 10 ml of 0.1N carbonate buffer, pH 8 maintained in an ice bath. The solution was stirred at room temperature for 3 hours, then dialyzed at 4° C. against $3 \times 1$ L of 50 mM carbonate buffer, pH 8 containing 150 mM NaCl over 24 hours. The extent of conjugation as judged by the incorporation of $^{14}C$ labelled Compound I into BSA, determined from aliquots removed before and after dialysis, was found to be 18:1 (Compound I:BSA).

BALB/c mice were immunized with three injections of 35 µg of immunogen at 3 to 4 week intervals. All injections were intraperitoneal using immunogen emulsified for the first dose in complete Freund's adjuvant, and for all subsequent injections in incomplete Freund's adjuvant. Mice were immunized at 3 to 4 week intervals, tail bled and the resultant sera analyzed for the presence of antibodies recognizing Compound I by both RIA and ELISA. Mice having the highest serum titers (those mice whose serum could be diluted 500-fold and still bind greater than 50% of radiolabel based on the RIA described in Example IV) were selected for fusions. Mice selected for fusion were immunized with 150 µg of immunogen in 55 mM sodium phosphate buffer, pH 7.3 containing 150 mM NaCl (PBS) for three successive days followed by one day with no exposure to immunogen just prior to performing a fusion.

Fusions were performed according to a modification of the method of Kohler and Milstein, Nature, 256, 495-497 (1975), using PEG 4000 obtained from Gibco. SP$_2$/O myeloma cells and spleen cells from selected mice were washed 3 times with DMEM (serum free) and collected by centrifugation. The collected cells were counted, mixed at a ratio of $10^8$ spleen cells to $2 \times 10^7$ myeloma cells in a 50 ml sterile tube and centrifuged for 5 minutes at 1000 rpm. The entire supernatant was removed with a sterile 5 or 10 ml pipette. 1.0 ml of PEG (50% PEG 3,000 to 4,000, Gibco Laboratories) was slowly added to the pelleted cells with mixing over 1 minute, and the resulting cell suspension was incubated, while slowly mixing by hand, in a water bath at 37° C. for 2 to 3 minutes. 2.0 ml of DMEM (serum free) was then slowly added with mixing over a 2 to 3 minute period, after which 7.0 ml of DMEM (serum free) was slowly added over a 2 to 3 minute period. The cells were pelleted by centrifugation at 1000 rpm for 5 minutes. DMEM with 15% horse serum (10 ml) was released directly onto the pellet, and the pellet gently resuspended. 20 ml of DMEM complete containing 15% horse serum and supplemented with a 10-fold dilution of HCF (IGEN, Inc.) was then added, and the cells were resuspended, resulting in a cell suspension containing $4 \times 10^5$ myeloma cells/ml in complete media containing HAT and supplemented with HCF to promote cell growth (HAT selection media). Cells were then plated out in 96-well microtiter plates (150 µl/well) by adding to each well 100 µl of cell suspension and 50 µl of DMEM containing 10% fetal calf serum supplemented with HAT and HCF, and the microtiter plates were placed in a CO$_2$ incubator set at 37° C. After a 24 hour growth period, 100 µl of media was withdrawn from each well, and 100 µl of fresh DMEM containing 10% fetal calf serum supplemented with HAT and HCF was added back to each well. Clones growing in selection media in microtiter plate wells were identified by examining each well using an inverted light microscope. Media from wells containing these clones was then tested for the presence of specific antibody by RIA or ELISA.

EXAMPLE III

Expansion of Antibody Producing Hybridomas

Hybridomas producing specific antibody as demonstrated by RIA or ELISA were expanded by standard cell culture techniques and gradually transferred over a period of 3 to 4 weeks to media containing no aminopterin (HT selection media). Once the hybridomas were completely transferred to HT media they were gradually transferred over an additional period of 3 to 4 weeks to DMEM complete media. Expanded and subcloned hybridomas were grown in DMEM complete media in T-75 tissue culture flasks (Corning Glass Works, Corning, N.Y.), and media containing antibody harvested when cell growth reached confluency. When necessary, to obtain high concentrations of MCTX1, media from T-75 tissue culture flasks was concentrated using an Amicon ultrafiltration unit containing Diaflo XM50 ultrafilters (Amicon).

In addition to cell culture methods, hybridomas were also grown in the peritoneal cavity of syngeneic BALB/c mice. Mice were injected intraperitoneally with 0.5 ml of pristane. After 8 to 10 days, hybridomas ($2\times10^6$ cells in 100 μl sterile PBS) which were shown by RIA to secrete high concentrations of MCTX1 (greater than 50% binding of radiolabel using 50 μl of undiluted media in the RIA described in Example IV) were inoculated intraperitoneally into the pristine treated BALB/c mice to produce ascites fluid. Ascites fluid was removed from the mice after 2 to 3 weeks, and stored at −22° C. after the addition of Na-azide to a concentration of 0.1% until further use.

EXAMPLE IV

Radioimmunoassay (RIA)

Sera from immunized mice and media collected from wells containing HAT selected hybridomas were tested for the presence of antibodies recognizing Compound I by RIA. Undiluted media (50 μl) was incubated overnight at 4° C. with PBS (50 μl), normal human sera (50 μl) and [$^{125}I$]-iodohistamine - Compound I (radiolabel-1) in PBS (200 μl, 50,000 CPM). After incubation, 1.0 ml of PEG 8000 (Fisher Scientific, Fairlawn, N.J.) (25% wt/vol) was added as separant; samples were centrigued at room temperature at $2000\times g$ for 10 to 15 minutes and the supernatant decanted. Radioactivity associated with the precipitate was then determined using an APEX automatic gamma counter (ICN Micromedic Systems). Satisfactory zero binding and sensitivity were obtained after an overnight incubation at 4° C.

The structure of the radiolabel-1 used in this assay is shown in Table 1. In order to prepare radiolabel-1, a solution of Compound I (72.6 mg, 0.17 mmol), N-hydroxysuccinimide (67.9 mg, 0.6 mmol), and dicyclohexylcarbodiimide (DDC) (102.0 mg, 0.49 mmol) in 10 ml dimethylformamide was stirred at room temperature under argon gas for 2 hours. Histamine (76.3 mg, 0.69 mmol) and $Et_3N$ (90.4 mg, 0.89 mmol) was then added to the reaction mixture. After an additional two hours, a second portion of DDC (87.0 mg, 0.42 mmol) was added, and the reaction mixture stirred overnight at room temperature under argon. The reaction mixture was evaporated in vacuo to a residue and evaporated once from 20 ml $CH_3CN$. The residue was dissolved in 10 ml CH$_3$CN, filtered to remove urea, reduced in volume to 2.5 ml, and purified by preparative HPLC (Dynamax C$_{18}$, 2.14×25 cm; 0.1% TFA/CH$_3$CN (68:32); 15 ml/min; UV 215 nm; tr 15.0 min) to afford 47.9 mg (54%) of a colorless oil [MS (FAB+): 516 (M+H). Analysis Calculated for C$_{28}$H$_{45}$N$_5$O$_4$1.0TFA.1.25H$_2$O: C, 55.25; H, 7.50; N, 10.74. Found: C, 55.33; H, 7.41; N, 10.34].

To a solution of the colorless oil (20 μg, 0.04 μmol) dissolved in 20 μl of MeOH was added 10 μl (5 mCi) of Na$^{125}$I followed by 20 μl (0.14 μmol) of a 7.1 mM solution of chloramine-T dissolved in MeOH. After 1 minute, the reaction was quenched by the addition of 20 μl (0.32 μmol) of a 15.8 mM aqueous solution of Na$_2$S$_2$O$_5$. The reaction mixture was diluted with 100 μl of MeOH and subjected to HPLC (C$_{18}$, 4.6×250 mm; 0.1% TFA:CH$_3$CN (65:35); 1.0 ml/min; radiometric detection; t$_r$ 31.5 min).

In order to assay samples for thromboxane A2 receptor antagonist, the same procedure was used, except that 50 μl of sample was used in place of the 50 μl of PBS.

In this regard, for construction of the standard curve and determination of cross-reactivity, standards and cross-reactants were prepared in PBS. Three cross-reactants were examined: the dinor and tetranor, possible metabolites of Compound I, and a related compound, Compound II, which lacks most of the omega side chain (Table 2).

TABLE 2
STRUCTURES OF COMPOUND I, ITS POTENTIAL METABOLITES AND COMPOUND II

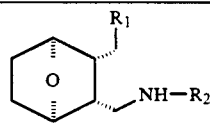

| COMPOUND | R$_1$, R$_2$ |
|---|---|
| Compound I | R$_1$ = —CH=CH—CH$_2$—CH$_2$—CH$_2$—COOH |
| | R$_2$ = —COCH$_2$—NH—CO-Hexyl |
| Dinor | R$_1$ = —CH=CH—CH$_2$—COOH |
| | R$_2$ = —COCH$_2$—NH—CO-Hexyl |
| Tetranor | R$_1$ = —CH$_2$—COOH |
| | R$_2$ = —COCH$_2$—NH—CO-Hexyl |
| Compound II | R$_1$ = —CH=CH—CH$_2$—CH$_2$—COOCH$_3$ |
| | R$_2$ = —H(HCl Salt) |

EXAMPLE V

Enzyme-Linked Immunosorbent Assay (ELISA)

Sera from immunized mice or media from wells containing cell colonies growing in selection media were assayed by indirect ELISA for the presence of antibodies recognizing Compound I. Thyroglobulin conjugated Compound I was plated on 96-well polystyrene microtiter plates (Immulon I Flat Bottom Plates, Dynatech Laboratories) at a concentration of 5 μg/well in a volume of 30 μl. After drying the plates for 1 hour in an oven set at 50° C., each well was filled with 300 μl of 55 mm Tris-HCl, pH 7.8 containing 150 mM NaCl (TBS) and 0.1% gelatin (bloom 300) (Sigma Chemical Co., St. Louis, Mo.) and allowed to stand for 1 hour at room temperature. Media (100 μl) containing MCTX1 was added to each well and incubated overnight at 4° C. Each well was then washed 8 to 10 times with 150-200 μl of TBS containing 0.1% Tween 20. To detect the presence of the primary antibody (MCTX1), 100 μl of an affinity purified goat anti-mouse (H +L) horseradish peroxidase (HRP) conjugated second antibody (1:500 dilution in TBS) (Organon Teknika-Cappel, One Technology Court, Malvern, Pa.) was added to each well followed by an overnight incubation at 4° C. Each well of the plates was then extensively washed 8 to 10 times with about 150 to 200 μl TBS containing 0.1% Tween 20. The colorimetric product was visualized within 20 minutes of adding 100 μl of a substrate solution containing 0.5 mg/ml ABTS (2,2'-azino-bis(3-ethylbenzthiazoline-6-sulfonic acid) and 0.01% H$_2$O$_2$ in 0.1M citrate buffer, pH 4.1 to each well. The reaction product was measured at 410 nm using a Dynatech MR 700 microtiter plate reader (Dynatech Laboratories, Inc., Chantilly, Va.).

In order to assay samples thought or known to contain a thromboxane A$_2$ receptor antagonist, the same procedure is used except that sample is also added to the microtiter plate before the overnight incubation at 4° C.

To prepare the thyroglobulin conjugated Compound I used in this assay, a sample of Compound I (9.9 mg, 2.3×10$^{-2}$ mmol) spiked with $^{14}$C labeled Compound I (1.1 mg, 2.7×10$^{-3}$ mmol) was dissolved in 0.5 ml of dimethylformamide and cooled in an ice bath. To this was added N-hydroxysuccinimide (6.1 mg, 5.3×10$^{-2}$ mmol) and 1-ethyl-3-(3-dimethylaminopropyl)carbodiimide (10.1 mg, 5.3×10$^{-2}$ mmol). The resulting solution was brought to room temperature and stirred for 2 hours, then added dropwise to a solution of heat-treated thyroglobulin (20.0 mg, 3.1×10$^{-4}$ mmol) dissolved in 10 ml of 0.1N carbonate buffer, pH 8 maintained in an ice bath. The solution was stirred at room temperature for 3 hours, then dialyzed at 4° C. against 3×1 L of 50 mM carbonate buffer, pH 8 containing 150 mM NaCl over 24 hours.

EXAMPLE VI

Sub-Isotyping

To determine the immunoglobulin class/subclass type of MCTX1, antibody containing media was assayed with an ELISA based assay following the protocol accompanying a Mouse-Typer Sub-Isotyping Kit (BIO-RAD Isotyping panel 172-2055, Bio-Rad Laboratories, Hercules, Calif.).

EXAMPLE VII

Monoclonal Antibody Purification

About 2 to 4 ml of ascites fluid containing MCTX1 was diluted 1:1 with PBS and applied to a 1.5 cm×100 cm CM Affi-Gel Blue column (Bio-Rad Laboratories, Hercules, Calif.) pre-equilibrated with PBS. Fractions (2.0 ml) were collected at a flow rate of 0.5 ml/minute and protein eluting from the column was monitored by determining the absorbance at 280 nm for each sample. The elution of MCTX1 from the column was monitored using the RIA described above. Chromatography was performed at room temperature. Fractions containing MCTX1 were pooled, dialyzed overnight at 4° C. against 55 mM sodium phosphate, pH 7.0 and concentrated using Aquacide II (Calbiochem). The resultant sample was adjusted to pH 5.5 with 0.1M glycine, pH 2.5 and applied to a 1.5 cm×8.0 cm recombinant-Protein G Sepharose 4B column (ZYMED Laboratories, San Francisco, Calif.) pre-equilibrated with 0.1M sodium phosphate, pH 5.5. The column was then washed with 50 ml of 0.1M sodium phosphate, pH 5.5 at a flow rate 0.5 ml/minute. Bound MCTX1 was eluted from the column by washing the column with 15 ml of 0.1M glycine, pH 9.5 at a flow rate of 0.5 ml/minute. Chromatography was performed at room temperature. Fractions (1.0 ml) were collected in test tubes containing 100 μl of 1.0M Tris buffer, pH 7.0, which neutralized the resultant samples. The protein concentration was calculated using an extinction coefficient for immunoglobulin of $\epsilon = 1.41$ cm$^2$/mg. MCTX1 was detected using the RIA described above and expressed as percent binding of radioligand.

EXAMPLE VIII

Analytical Methods

Sodium dodecyl sulfate-polyacrylamide gel electrophoresis (SDS-PAGE) was performed using a PHAST SDS-PAGE System (Pharmacia, Piscataway, N.J.). This system makes use of a 10% to 15% preformed gel and buffer systems essentially as described by Laemmli, U.K., "Cleavage of Structural Proteins During Assembly of the Head of Bacteriophage T$_4$", *Nature*, 227:680–685 (1970). Samples of 1 to 5 μg were incubated with or without dithiothreitol for 5 to 10 minutes at room temperature to reduce disulfide bonds. The samples were then dissolved in SDS, heated and subjected to electrophoresis, as described in the Owner's Manual accompanying the PHAST System.

High pressure liquid chromatography (HPLC) was performed using a Beckman System Gold analog interface module 406. Samples were subjected to isocratic HPLC using a TSK G3000SW column (7.5 mm ID × 30 cm) eluted with 0.05 mM sodium phosphate buffer, pH 6.5 at a flow rate of 1.0 ml/minute. Protein was monitored at 280 nm and the relative molecular weight of MCTX1 determined by comparing its retention time with that of gel filtration molecular weight markers (Sigma Chemical Company, St. Louis, Mo.) previously run through the column under identical conditions.

EXAMPLE IX

Identification and Characterization of MCTX1

Mice immunized with Compound I-BSA had detectable levels of Compound I antibody three months after initiating immunization. Sera from each mouse was tested at three different dilutions by RIA for the presence of antibodies recognizing Compound I. Of the twelve mice immunized, eight bound greater than 50% of the radioligand using sera diluted 1:100, whereas six animals bound greater than 50% of the radioligand even at a sera dilution of 1:500. Only one animal lacked any detectable Compound I antibody.

Mice having the highest serum titers were selected and used for fusions as described above. Three weeks after the fusions, HAT selected clones were distinguished by light microscopy and antibody producing hybridomas identified by RIA. One hybridoma, designated HYTX, began producing high levels of Compound I antibody (MCTX1) and continued to do so during expansion of the clone. Once the MCTX1 producing hybridoma was propagated to confluency in T-75 tissue culture flasks, a more detailed study of the properties of MCTX1 was undertaken. As a first step in such an analysis, a titration curve for the antibody was produced to determine the relative concentration of MCTX1 present in tissue culture media. Media containing antibody was used directly or concentrated 10-fold using an Amicon Diaflo XM50 ultrafilter system (operating under 20 psi of nitrogen pressure). 50% binding of radiolabel-I was obtained when antibody containing media was diluted 1:5 with PBS. For all subsequent RIAs, media was used at dilutions yielding 50% radioligand binding.

A standard curve constructed using MCTX1 has a range of 0 to 250 ng/ml of Compound I with a low detection limit of 5 ng/ml (FIG. 1). The competitive nature of such a curve demonstrates the binding of MCTX1 to Compound I in addition to its corresponding radiolabel.

To further characterize the specific structural features (epitope) within Compound I that are recognized by MCTX1, various derivatives of Compound I were tested for their cross-reactivity. The percent cross-reactivity was determined by dividing the ED$_{50}$ of Compound I into the ED$_{50}$ of the cross-reactants and multiplying the result by 100. The structures of derivatives of Compound I which were evaluated are shown in Table 2. Compound II, a compound lacking most of the omega-side chain, was not recognized by MCTX1. Two potential metabolites of Compound I, the dinor and tetranor derivatives, had cross-reactivities of 66% and 17.6%, respectively. Both of these compounds have shortened alpha-side chains and no modifications in their omega-side chain. The extent of cross-reactivity of both alpha-side chain metabolites became less as the alpha-side chain became more truncated. Therefore, modifications in both the alpha-side chain and the omega-side chain of Compound I appear to alter the epitope recognized by MCTX1.

EXAMPLE X

Affinity Purification of MCTX1

Hybridomas secreting MCTX1 were inoculated into pristane-treated BALB/c mice to produce ascites fluid which was used as starting material for the isolation of MCTX1. Ascites fluid was collected from four different mice and the amount of MCTX1 present was titrated by RIA. All four mice produced ascites fluid containing MCTX1 at concentrations significantly greater than that found in antibody containing media. Ascites fluid from all four animals was pooled and used as starting material to isolate MCTX1.

Ascites fluid was diluted 1:1 with 2 × PBS and applied to a CM Affi-Gel Blue column as described above. Column fractions were collected and the distribution of protein determined by UV absorption (280 nm) and MCTX1 by RIA. CM Affi-Gel Blue chromatography removes albumin, complement proteins, and serum proteases from the sample, thereby enriching the fraction for MCTX1. Serum proteins such as these bind to the column whereas immunoglobulins do not. MCTX1 therefore elutes after the void volume. Protein was detected beginning with fraction 10 and ending at fraction 20. Both protein and MCTX1 began eluting from the column at the same time. However, MCTX1 continued to emerge from the column during a time when protein could not be detected by UV absorption spectroscopy. Fractions 14 to 24 containing enriched MCTX1 were collected, pooled, concentrated, and dialyzed against 0.1M sodium phosphate buffer, pH 7.0. After concentration and adjustment of the sample to pH 5.5, the resultant sample was applied to a Sepharose 4B conjugated recombinant Protein G column pre-equilibrated with 0.1M sodium phosphate, pH 5.5 as described above. The bulk of the protein eluted from the Protein G affinity column immediately after the void volume. MCTX1, however, was eluted by washing the column with 0.1M glycine, pH 9.5. A small amount of MCTX1 co-eluted with the first protein peak, and may reflect the presence of a population of MCTX1 having an altered Fc region or a limitation in the binding capacity of the protein G affinity column. Only fractions eluting from the affinity column after washing with alkaline buffer were collected. Fractions containing this form of MCTX1 were pooled, concentrated and dialyzed against PBS before analysis by HPLC and SDS-PAGE.

EXAMPLE XI

Characterization of Affinity Purified MCTX1

MCTX1 was shown to be of $IgG_1$ subclass by making use of an isotyping kit based on ELISA as described above. MCTX1 light chain designation could not be conclusively determined. Purified MCTX1 was subjected to HPLC and separated using a TSK G3000SW gel exclusion column. One major peak eluted from the column with a retention time of 6.68 minutes. This retention time was similar to the retention time calculated when a purified monoclonal antibody B72.3 (IgG) was analyzed under identical conditions. Calculations based on HPLC data were used to determine a relative purity of 94.0% for MCTX1. A small peak of unknown identity having a retention time of 10.08 minutes also eluted from the column.

In addition to HPLC, affinity purified MCTX1 was subjected to SDS-PAGE under non-reducing (-dithiothreitol) or reducing (+dithiothreitol) conditions. A single polypeptide of $M_r$ 155 Kd was present when MCTX1 was subjected to non-reducing SDS-PAGE. The molecular weight of this protein is in agreement with the expected molecular weight of intact IgG immunoglobulins. No other proteins were visualized within the gel when protein was stained with Coomassie blue R-250. MCTX1 analyzed under reducing conditions appeared as two polypeptides of $M_r$48 Kd and $M_r$ 23 Kd, respectively. These two polypeptides represent both the heavy chain ($M_r$48 Kd) and light chain ($M_r$23 Kd) of MCTX1.

DETAILED DESCRIPTION OF THE DRAWINGS

FIG. 1: Standard curve for MCTX1. B/Bo is a measure of the binding of radiolabel-1 by MCTX1 relative to the total amount of radiolabel-1 added minus the non-specific binding.

What is claimed is:

1. A hybridome cell line that produces a monoclonal antibody which binds the thromboxane $A_2$ receptor antagonist [1S-[1β,2α(5Z),3α,4β]]-7-[3-[[[[(1-oxoheptyl)amino]acetyl]amino]methyl]-7-oxabicyclo[2.2.1-]hept-2-yl]-5-heptenoic acid or a derivative thereof wherein said derivative has the following formula:

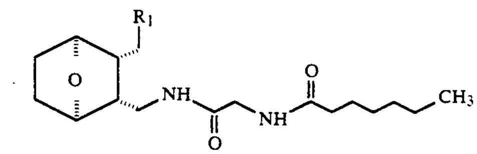

wherein $R_1$ is $—CH=CH—CH_2—COOH$, $—CH_2—COOH$,  , or

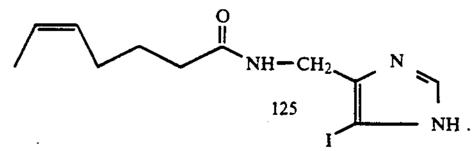

2. The hybridoma cell line according to claim 1 designated end having A.T.C.C. Accession Number HB 10235.

3. A hybridoma cell line having all of the identifying characteristics of the hybridoma cell line according to claim 2.

4. The monoclonal antibody secreted by the hybridoma cell line according to claims 2 or 3.

5. A monoclonal antibody secreted by the hybridoma cell line according to claim 1.

6. The monoclonal antibody according to claim 5 which is of the class IgG.

7. The monoclonal antibody according to claim 5 which is a murine monoclonal antibody.

8. The monoclonal antibody according to claim 5 designated MCTX1.

9. A monoclonal antibody having all of the identifying characteristics of the monoclonal antibody according to claim 8,

10. The monoclonal antibody according to claims 5 or 8 which has been derivatized by labeling with a detectable marker.

11. The monoclonal antibody according to claim 10 wherein the detectable marker is a radioisotope.

12. The monoclonal antibody according to claim 11 wherein the radioisotope is selected from the group consisting of $^{125}I$ or $^{131}I$.

13. The monoclonal antibody according to claim 10 wherein the detectable marker is an enzyme.

14. The monoclonal antibody according to claims 5 or 8 which has been purified.

15. An antigen 30 binding fragment of the monoclonal antibody according to claims 5 or 8.

* * * * *